(12) United States Patent
Nesbitt et al.

(10) Patent No.: US 10,470,859 B2
(45) Date of Patent: Nov. 12, 2019

(54) STERILE DENTAL SETUP PACK

(71) Applicants: Paula Evette Nesbitt, Hopewell, VA (US); Jarrett Anthony Scott, Brooklyn, NY (US)

(72) Inventors: Paula Evette Nesbitt, Hopewell, VA (US); Jarrett Anthony Scott, Brooklyn, NY (US)

( * ) Notice: Subject to any disclaimer, the term of this patent is extended or adjusted under 35 U.S.C. 154(b) by 94 days.

(21) Appl. No.: 15/292,971

(22) Filed: Oct. 13, 2016

(65) Prior Publication Data

US 2018/0104035 A1    Apr. 19, 2018

(51) Int. Cl.
| | |
|---|---|
| *A61C 19/02* | (2006.01) |
| *A61C 17/08* | (2006.01) |
| *A61B 13/00* | (2006.01) |
| *A61C 17/02* | (2006.01) |
| *A61F 13/38* | (2006.01) |

(Continued)

(52) U.S. Cl.
CPC .............. *A61C 19/02* (2013.01); *A61B 13/00* (2013.01); *A61C 3/00* (2013.01); *A61C 17/0217* (2013.01); *A61C 17/08* (2019.05); *A61F 13/38* (2013.01); *A61G 15/14* (2013.01); *A61C 2202/00* (2013.01); *A61C 2204/005* (2013.01); *A61C 2204/007* (2013.01); *A61G 2203/36* (2013.01)

(58) Field of Classification Search
CPC ... A61C 19/02; A61C 17/0217; A61C 17/043; A61C 17/08; A61C 3/00; A61C 2202/00; A61C 2204/005; A61C 2201/007; A61F 13/38; A61G 15/16; A61B 13/00

USPC ......................................................... 206/369
See application file for complete search history.

(56) References Cited

U.S. PATENT DOCUMENTS

| | | | |
|---|---|---|---|
| 3,137,387 A | 6/1964 | Overment | |
| 4,944,427 A | 7/1990 | Yamada et al. | |

(Continued)

FOREIGN PATENT DOCUMENTS

| | | |
|---|---|---|
| CN | 102335047 | 2/2012 |
| CN | 204181732 | 3/2015 |

(Continued)

OTHER PUBLICATIONS

Single Use Dental Examination Kit, Kencap Medical Solutions Ltd, http://www.kencap.info/examiantion-tray-kit/, 2012, (2 pages).

(Continued)

*Primary Examiner* — Chun Hoi Cheung
(74) *Attorney, Agent, or Firm* — Pilloff Passino & Cosenza LLP; Martin J. Cosenza

(57) ABSTRACT

A system and method for forming a sterile dental pack is disclosed. The method includes preparing a first wrap and a second wrap; arranging a plurality of dental disposable supplies on the first wrap; and wrapping the plurality of dental disposable supplies within the first wrap and the second wrap to form an airtight container. Also disclosed is a sterile dental pack dispensing system. The sterile dental pack dispensing system may include a storage container with an opening, the storage container being configured to store a wrapped sterile dental pack; an output configured to receive the wrapped sterile dental pack from the storage container; and a fiber optic indicator configured to cause the wrapped sterile dental pack to move from the storage container to the output through the opening.

12 Claims, 8 Drawing Sheets

(51) Int. Cl.
*A61G 15/14* (2006.01)
*A61C 3/00* (2006.01)

(56) References Cited

U.S. PATENT DOCUMENTS

| | | | |
|---|---|---|---|
| 5,031,768 A | 7/1991 | Fischer | |
| 5,804,512 A | 9/1998 | Lickfield et al. | |
| 6,206,192 B1* | 3/2001 | Winstead | A61C 19/02 |
| | | | 206/369 |
| 6,312,258 B1 | 11/2001 | Ashman | |
| 6,341,694 B1 | 1/2002 | Dawood | |
| 6,406,764 B2* | 6/2002 | Bayer | A61L 2/07 |
| | | | 206/438 |
| 6,517,916 B1* | 2/2003 | Bayer | A61L 2/26 |
| | | | 428/34.3 |
| 6,715,603 B1 | 4/2004 | Uribe | |
| 7,153,469 B2* | 12/2006 | Bayer | A61L 2/26 |
| | | | 422/1 |
| 8,177,064 B2 | 5/2012 | McCormick et al. | |
| 2002/0193517 A1* | 12/2002 | Wang | C08L 51/00 |
| | | | 525/63 |
| 2002/0197424 A1* | 12/2002 | Bayer | A61L 2/26 |
| | | | 428/34.2 |
| 2004/0074593 A1 | 4/2004 | Schild et al. | |
| 2005/0079093 A1* | 4/2005 | Cannady | B32B 7/05 |
| | | | 422/1 |
| 2006/0104856 A1* | 5/2006 | Farrell | A61L 2/07 |
| | | | 422/1 |
| 2007/0026472 A1* | 2/2007 | Prokash | A61L 2/07 |
| | | | 435/7.32 |
| 2007/0095699 A1* | 5/2007 | Frieze | A61L 2/07 |
| | | | 206/438 |
| 2011/0079535 A1* | 4/2011 | Prokash | A61L 2/07 |
| | | | 206/524.6 |
| 2013/0092724 A1 | 4/2013 | Gaynor et al. | |

FOREIGN PATENT DOCUMENTS

| | | |
|---|---|---|
| DE | 8803716 | 6/1988 |
| FR | 2646770 | 11/1990 |
| WO | 1996007364 | 3/1996 |

OTHER PUBLICATIONS

Sterile Single Use Dental Instrument Kits, MDDI, https://www.mddiglobal.com/dental-instrument-kits/, 2015, (2 pages).
Sterile Pack Disposable Surgery Kits—Dental, NivMedical, https://www.youtube.com/watch?v=HMPr9i3y0IA, Mar. 2014, (2 pages).
Notification of Transmittal of the International Search Report and the Written Opinion of the International Searching Authority, or the Declaration, International Search Report and Written Opinion of the International Searching Authority, dated Jan. 25, 2018 and received in related PCT Application No. PCT/US17/56312.

* cited by examiner

STERILE DENTAL SETUP PACK

TECHNICAL FIELD

This disclosure is generally related to dental procedures. More specifically, this disclosure is related to a wrapped, sterilized package containing a variety of dental disposable supplies that may be used during a dental procedure.

BACKGROUND

Currently, when a dentist or other oral care professional prepares to perform a dental procedure, dental disposable supplies that are used to carry out the dental procedure may be individually retrieved, which increases the likelihood of cross contamination. In some procedures, eleven, or even more, dental disposable supplies may be necessary to complete a procedure. Finding, collecting, and placing all of the necessary dental disposable supplies may be a time-consuming process because the disposable supplies may not all be located in the same area in a dental office. Occasionally, one of the disposable supplies needed for the procedure may be forgotten. This may make an already time-consuming process even longer. Moreover, if the dentist or other oral care professional is already carrying out the procedure, retrieving a missing dental disposable item may increase the stress level of both the dentist and the patient. The patient may also become less confident about the dental office or the procedure as the assistant searches for the needed component.

Most importantly, cross-contamination is a serious issue that must be prevented for each procedure. As patients have become more knowledgeable about dental procedures, patients have become more aware of cross-contamination issues. For example, if an assistant has to retrieve a missing disposable item, the chain of infection control may be broken. The assistant may unknowingly and/or unintentionally contaminate the retrieved missing dental disposable item. This contaminated item may then be placed within a dental operating field, such as the inside of a patient's mouth. This may lead to viral or bacterial infection, and/or disease that could have been avoided if all of the necessary dental disposable supplies had been collected in one place and sterilized as an infection control measure before the procedure began. In dentistry, all dental instruments that are placed in a patient's mouth are sterilized, reused, and recycled. An instrument used in the practice of dentistry includes a variety of hand or machine-driven cutting instruments for soft and calcified tissues, forceps, elevators, clamps, reamers, wire pliers, pluggers, carvers, explorers, and other instruments unique to the dental specialties, such as oral surgery, endodontics, orthodontics, periodontics, prosthodontics, and restorative dentistry. Although dental disposable supplies are designed to be used once, discarded, and not reused or recycled as an infection control measure, they are placed in a patient's mouth unsterilized. The unsterilized dental supplies are stored in areas that are exposed to dental procedure aerosol contamination from air droplets of contaminated water that may be mixed with, for example, blood, saliva, and diseases created or exposed during dental procedures and/or direct contamination by personnel who may not have completely disinfected surfaces that store the unsterilized items that are eventually placed in a patient's mouth. Infective agents may be transmitted via aerosol droplets to patients and staff. The aerosol bacterial/viral contamination is produced during the use of dental scalers and dental equipment that produces an aerosol spray. Additionally, many patients pass through a dental operatory. Such patients may have been unknowingly exposed to, for example, HIV, Hepatitis, TB, flu viruses, bacterial, and fungal contamination that is in their saliva or blood. This is the reason for vigilant hand washing and use of universal precautions such as masks, eyewear, gloves, and gowns to protect practitioners as well as the next patient that is treated.

Sterile dental packs are an additional universal precaution to protect the patient that is treated by providing an additional protection barrier and is the answer to the dilemma of cross-infection/cross-contamination in the practice of dentistry.

By minimizing risk of or avoiding cross-contamination, patients would have more confidence in the dental procedure and, therefore, be less stressed. Moreover, even one cross-contamination incident may damage a reputation of the dentist or oral care professional. Additionally, an infection due to cross-contamination may lead to a malpractice lawsuit. Therefore, it is in the interests of both patients and dentists or oral care professionals to minimize or eliminate cross-contamination.

Accordingly, there is a need for a convenient and sterilized set of dental disposable supplies for use in dental procedures for the purpose of infection control.

SUMMARY

In one aspect of this disclosure, a system including a first wrap, a second wrap, and a plurality of dental disposable components arranged on top of the first wrap, which partially encloses the plurality of disposable components; the second wrap completely encloses the first wrap and dental disposable components within the first wrap is disclosed.

In another aspect of this disclosure, a system including a storage container with an opening, the storage container being configured to store a wrapped sterile dental pack, and an output configured to receive the wrapped sterile dental pack from the storage container is disclosed.

In another aspect of this disclosure, a method including preparing a first wrap and a second wrap, arranging a plurality of dental disposable components on the first wrap, and wrapping the plurality of components within the first wrap and the second wrap is disclosed.

DETAILED DESCRIPTION

Figure 1:
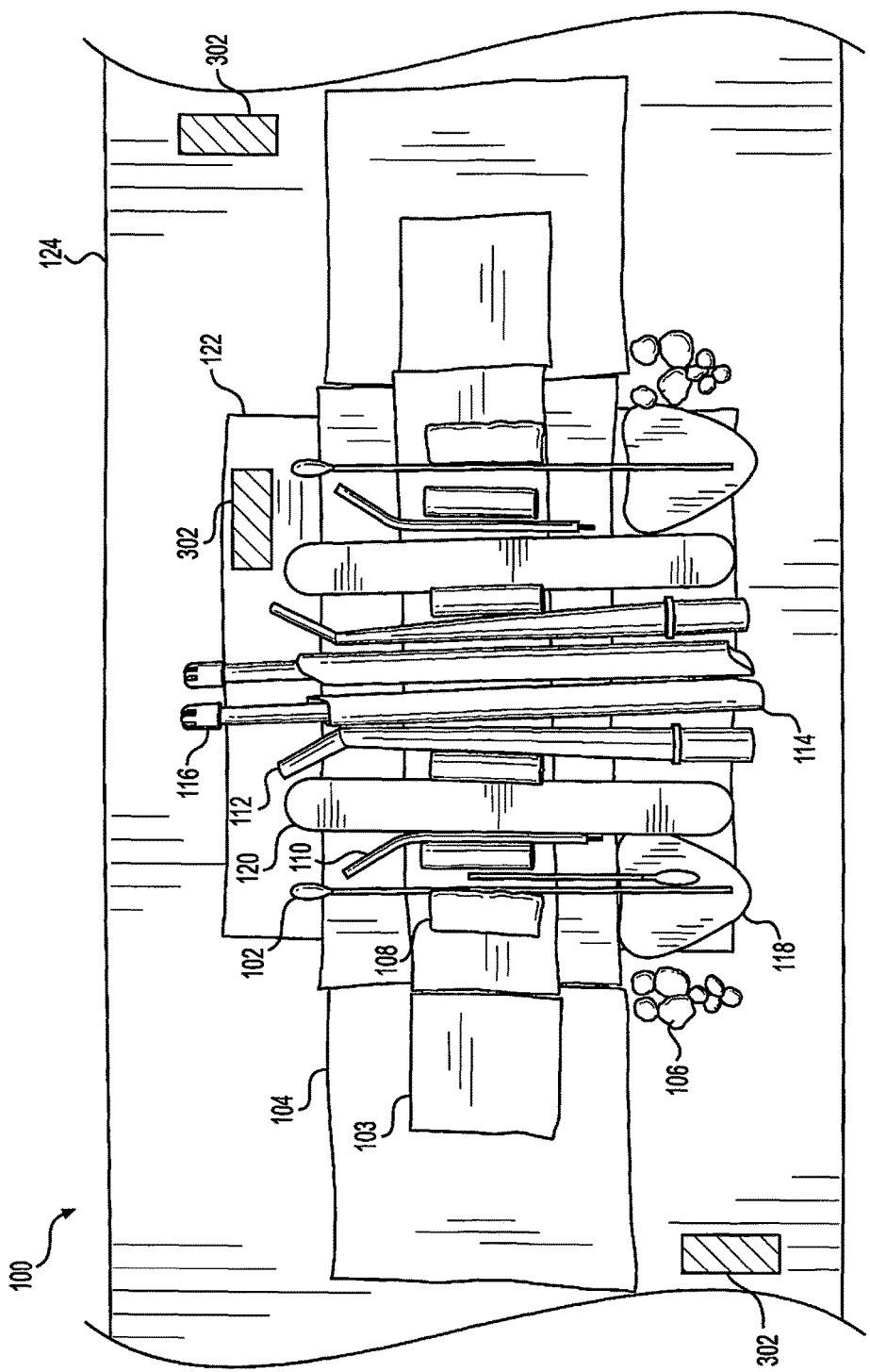
FIG. 1 shows a sterile dental pack, according to one aspect of this disclosure.

It is to be understood that the figures and descriptions of the present disclosure may have been simplified to illustrate elements that are relevant for a clear understanding of the present disclosure, while eliminating, for purposes of clarity, other elements found in a typical networking system or method. Those of ordinary skill in the art will recognize that other elements may be desirable and/or required in order to implement the present disclosure. However, because such elements are well known in the art, and because they do not facilitate a better understanding of the present disclosure, a discussion of such elements is not provided herein. It is also to be understood that the figures included herewith only provide diagrammatic representations of the presently preferred structures of the present disclosure and that structures falling within the scope of the present disclosure may include structures different than those shown in the drawings.

Broadly, this disclosure is related to a wrapped sterile dental pack. A plurality of dental disposable supplies may be arranged on a first wrapping material with an adhesive sterile indicator for, for example, Ethylene Oxide gas attached on the right and left corners of the first and second wraps, for example. The plurality of supplies may be arranged parallel to each, which may increase the number of disposable dental supplies contained in a wrapped sterile dental pack. After the disposable supplies are arranged on the first wrapping material, the first wrapping material may be held together by using an adhesive sterile indicator for, for example, Ethylene Oxide gas. A second wrapping material may be wrapped around the first wrapping material and the dental disposable supplies to enclose the first wrapping material and the disposable items and a sterile indicator for, for example, Ethylene Oxide gas may be attached. The first wrapping material that is wrapped around the disposable supplies may be a central supply room (CSR) tube made from CSR paper created as a thick covering that eases the rolling capacity of the sterile dental pack from the dispenser. In addition, the second wrapping material is CSR paper. The wrapped sterile dental pack provides an extra layer of protection from cross-contamination and cross-infection and is intended to serve as an addition to the infection control guidelines and protocols in the field of dentistry. Moreover, the wrapped sterile dental pack has a size and a shape that allows it to be stored with less space than the space required to individually store all the individual, separately packaged components.

The wrapped sterile dental pack may be placed within a wrapped sterile dental pack dispensing system. The dispensing system may include a storage, an output, and a fiber optic indicator. The wrapped sterile dental pack may be placed within the storage. When a user, such as an oral care professional, wishes to retrieve a wrapped sterile dental pack, the user may place a hand near the output. The fiber optic indicator may detect the hand and cause the dispensing system to dispense a wrapped sterile dental pack from the storage to the output.

FIG. 1 shows a sterile dental pack 100, according to one aspect of this disclosure. The sterile dental pack 100 shown in FIG. 1 is in an unwrapped state. The sterile dental pack 100 may include one or more cotton applicator sticks 102, one or more gauze sponges 103, 104, one or more cotton pellets 106, one or more cotton rolls 108, one or more air water syringes 110, one or more surgical suction tips 112, one or more high volume suction tips 114, one or more saliva ejectors 116, one or more parotid salivary control pads 118, one or more tongue depressors 120, and two CSR wraps 122, 124. For example, in one aspect of this disclosure, there may be three (3) cotton applicator sticks 102. Two (2) of the cotton applicator sticks 102 may be, for example, six inches, and one (1) cotton applicator stick 102 may be, for example, three inches (other length cotton applicator sticks 102 may be included). Additionally, there may be two (2) four inches by four inches gauze sponges 104 and six (6) two inches by two inches gauze sponges 103. The gauze sponges 103, 104 may be woven or non-woven. There may be three (3) sizes of cotton pellets 106, such as size two, three, and four, which are industry standard sizes. The sterile dental pack 100 may also include a plurality of cotton rolls, e.g., six (6) cotton rolls 108. For example, two of the cotton rolls 108 may be braided and four of the cotton rolls 108 may be non-braided. The sterile dental pack 100 may also include two (2) air water syringes 110. Embodiments may also include two (2) surgical suction tips 112, one of which may be ¼" and one of which may be ¹⁄₁₆". There may also be two (2) high volume suction tips 114. One high volume suction tip 114 may be a vented combined tip while one high volume suction tip 114 may be a non-vented combined tip.

With continuing reference to FIG. 1, the sterile dental pack 100 may also include two (2) saliva ejectors 116, two (2) parotid salivary control pads 118, two (2) tongue depressors 120, and two (2) CSR wraps 122, 124. The CSR wrap 124 may be an external CSR wrap that may be, for example, 10 inches by twenty inches. A CSR wrap 122 may be an internal CSR wrap that may be, for example, 7 inches by 7 inches (shown in FIG. 3).

Additionally, the plurality of dental disposable supplies and the CSR wraps 122, 124 may be biodegradable. One of ordinary skill in the art would readily recognize that any number and any size of dental disposable supplies may be included within the sterile dental pack 100. Additionally, one of ordinary skill in the art would readily recognize that any type of dental disposable, not simply the ones listed above, may be found in the sterile dental pack 100. In addition, one of ordinary skill in the art would readily recognize that the sterile dental pack 100 may be used for all dental specialties as a set-up preparation, not simply one specialty.

Figure 2:
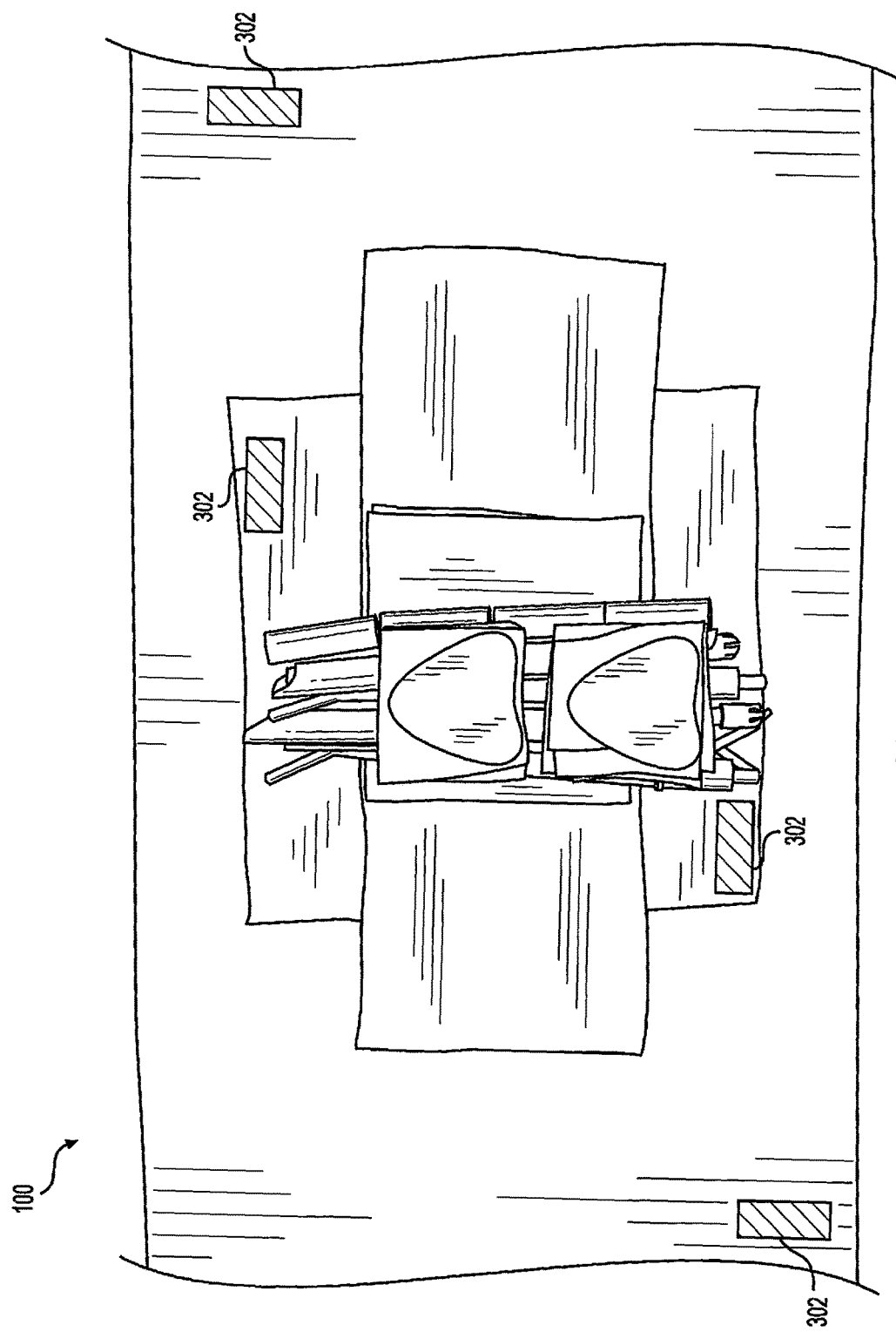
FIG. 2 shows a partially wrapped sterile dental pack, according to one aspect of this disclosure.

FIG. 2 shows a partially wrapped sterile dental pack 100, according to one aspect of this disclosure. In contrast to FIG. 1, the dental disposable supplies in FIG. 2 have been wrapped so that some dental disposable supplies may now rest on top of each other. In this wrapped configuration, sterile dental pack 100 may include two (2) or more layers of dental disposable supplies.

Figure 3:
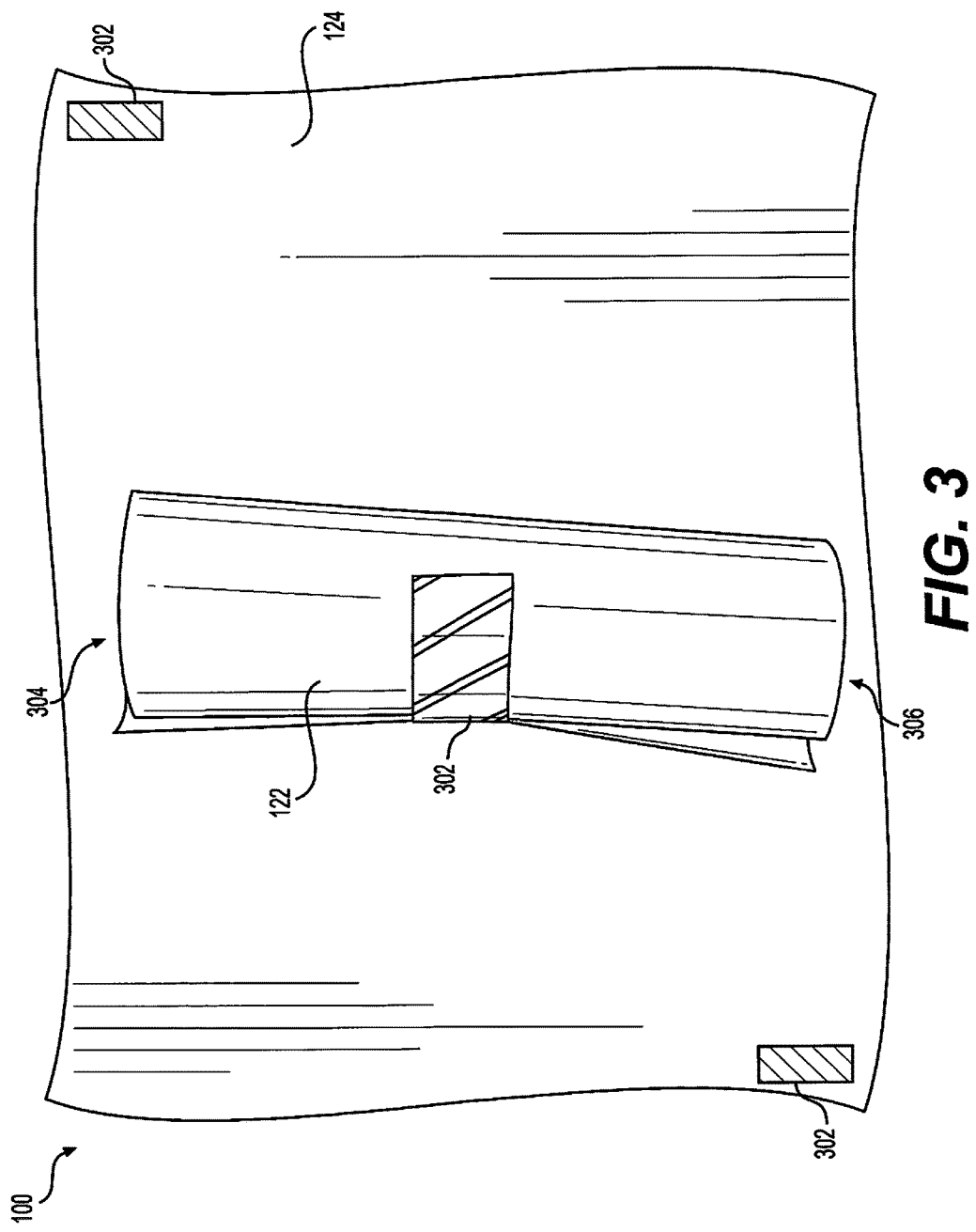
FIG. 3 shows the sterile dental pack wrapped by a first CSR wrap, according to one aspect of this disclosure.

FIG. 3 shows dental disposable supplies of the sterile dental pack 100 wrapped by the first CSR wrap 122 (internal CSR wrap), according to one aspect of this disclosure. FIG. 3 shows a continuation of the wrapping process of the sterile dental pack 100. FIG. 3 shows the sterile dental pack 100 wrapped by the first CSR wrap 122 and held together by at least one adhesive sterile indicator 302. The adhesive sterile indicator 302 may be an adhesive sterile indicator for Ethylene Oxide gas, which may be biodegradable. For example, the adhesive sterile indicator 302 may be a first color before the adhesive sterile indicator 302 is exposed to Ethylene Oxide gas and may change to a second color once the adhesive sterile indicator 302 has been exposed to Ethylene Oxide gas. A first end 304 and a second end 306 formed by the first CSR wrap 122 may be open. In other words, the first end 304 and the second end 306 may not be sealed closed.

Figure 4:
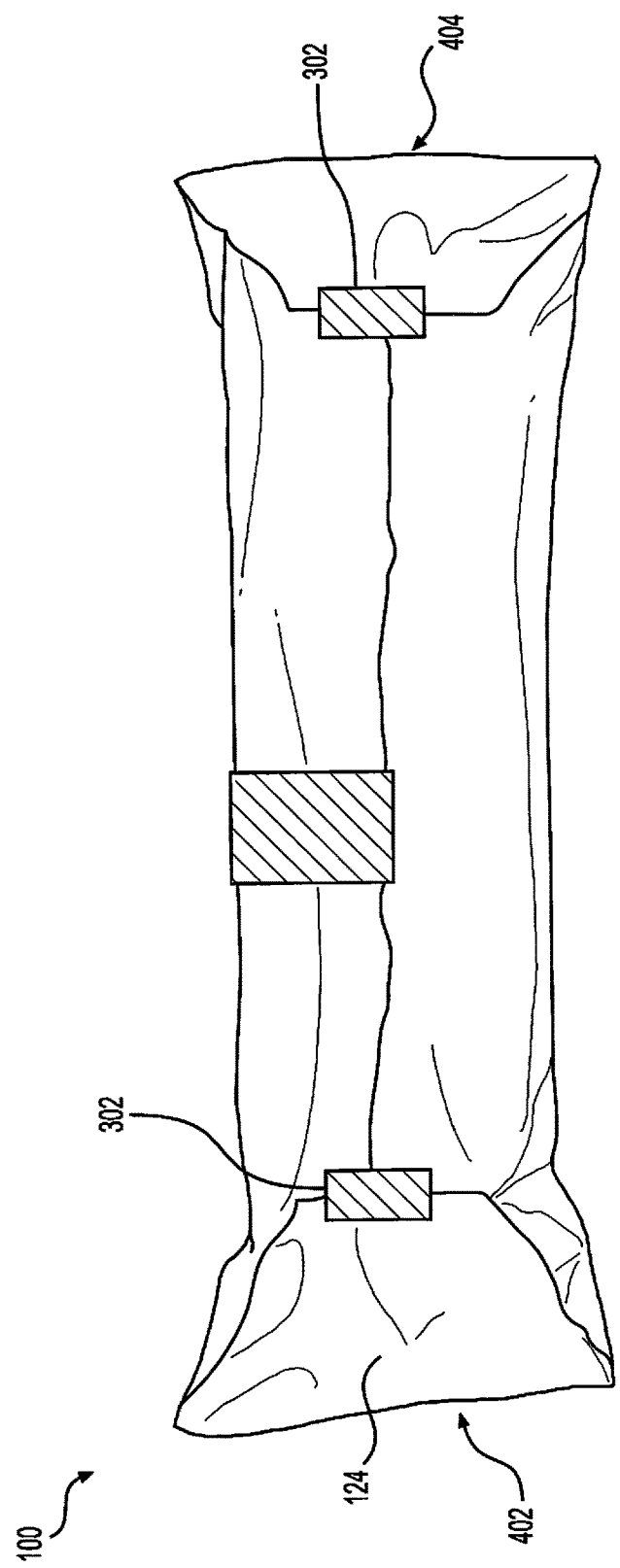
FIG. 4 shows a completely wrapped sterile dental pack, according to one aspect of this disclosure.

FIG. 4 shows a completely wrapped sterile dental pack 100, according to one aspect of this disclosure. In FIG. 4, the second CSR wrap 124 encloses the sterile dental pack 100 wrapped by the first CSR wrap 122, as shown in FIG. 3. The second CSR wrap 124 may, similarly to the first CSR wrap 122, be held together by one or more adhesive sterile indicators 302. The second CSR wrap 124 may have a first end 402 and a second end 404 that are sealed closed. An adhesive (not shown) may be used to seal the first end 402 and the second end 404. This may result in an airtight wrapped sterile dental pack 100.

Figure 5:
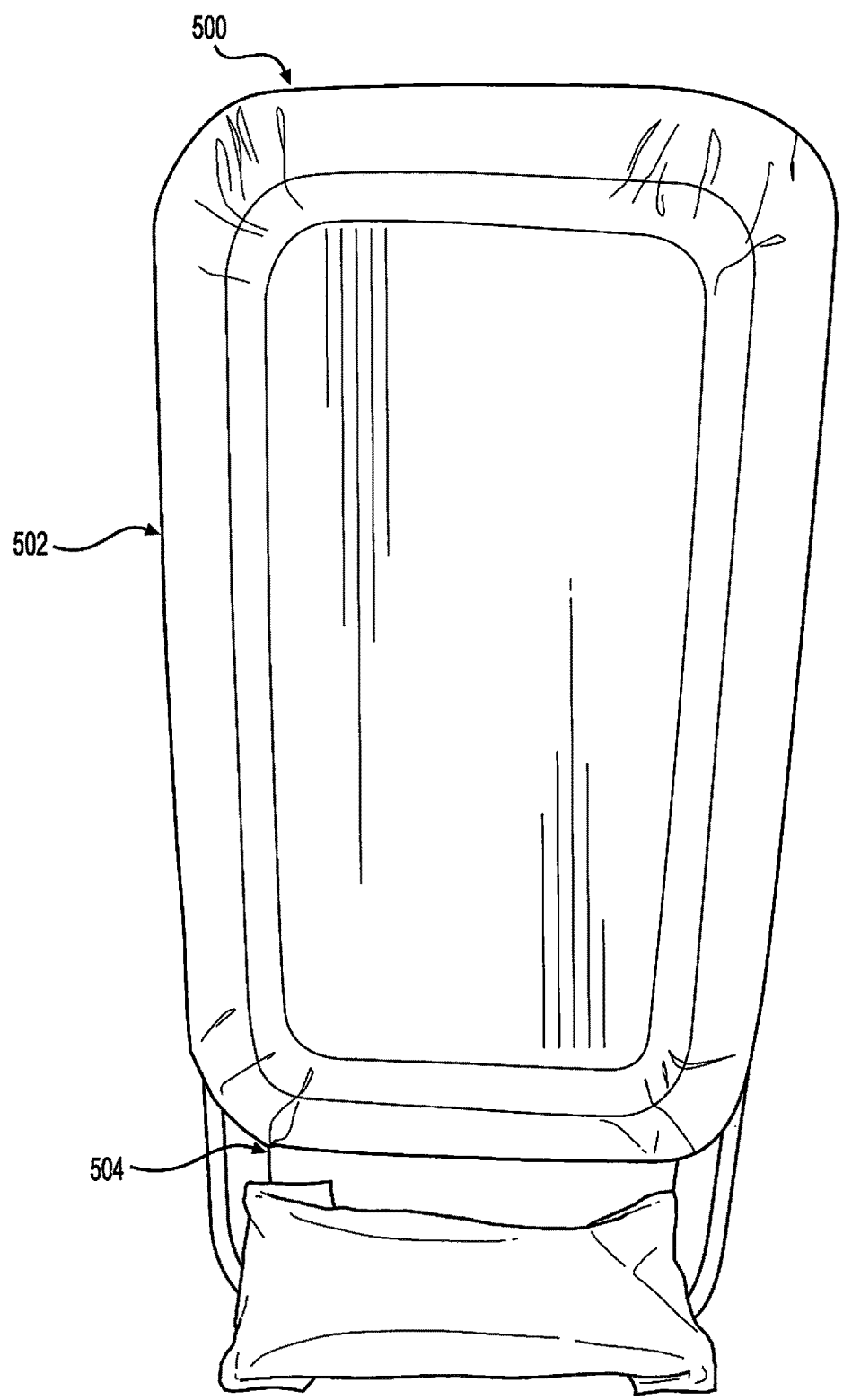
FIG. 5 shows a sterile dental pack dispensing system, according to one aspect of this disclosure.

FIG. 5 shows a sterile dental pack dispensing system 500, according to one aspect of this disclosure. The dispensing system 500 may include a dispensing system storage 502 and a dispensing system output 504. The dispensing system storage 502 may be any structure suitable to function as a storage container. For example, the dispensing system storage 502 may be a substantially rectangular container. The substantially rectangular container may be shaped to hold or store one or more wrapped sterile dental packs 100. The dispensing system 500 may also include the dispensing system output 504. The dispensing system output 504 may include an area where a wrapped sterile dental pack 100 may be available for collection. For example, there may be an opening within the dispensing system storage 502. The opening may approximate an outline of the wrapped sterile dental pack 100. A wrapped sterile dental pack 100 may be delivered from the dispensing system storage 502 to the dispensing system output 504. The delivery may happen upon actuation of a signal, as described below. The dispensing system output 504 may include a dispensing tray 602 (shown in FIG. 6). The dispensing tray 602 may receive the wrapped sterile dental pack 100 when the wrapped sterile dental pack 100 is delivered from the dispensing system storage 502 to the dispensing system output 504.

Figure 6:
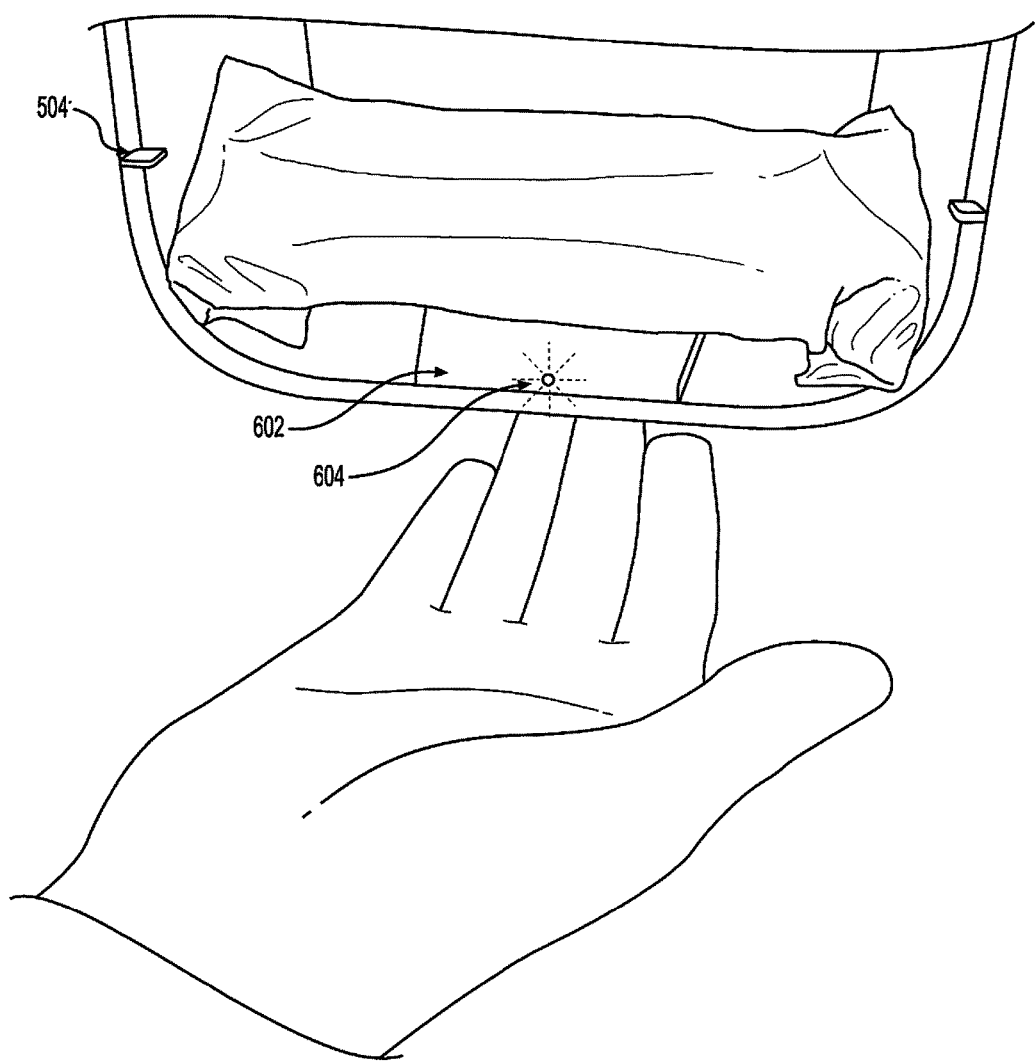
FIG. 6 shows the dispensing system output and a fiber optic indicator, according to one aspect of this disclosure.

FIG. 6 shows the dispensing system output 504 and a fiber optic indicator 604, according to one aspect of this disclosure. FIG. 6 more clearly shows the dispensing system output 504 and the dispensing tray 602. The dispensing tray 602 may be formed of any suitable material, such as various types of plastic. The sterile dental pack 100 may exit the dispensing system storage 502 and come to a rest within or on the dispensing tray 602. The sterile dental pack 100 may exit the dispensing system storage 502 because a user, such as the oral care professional, may actuate such an exit. For example, as shown in FIG. 6, the user may place a hand under the dispensing tray 602. This action may trigger the fiber optic indicator 604. The fiber optic indicator source may be located on or within the sterile dental pack dispensing system 500 and operatively connected to a mechanism in sterile dental pack dispensing system 500 that causes sterile dental pack 100 to be dispensed. When the fiber optic indicator 604 is triggered, for example, by a hand, the sterile dental pack dispensing system 500 may cause a wrapped sterile dental pack 100 to exit from or be dispensed by the dispensing system storage 502. Although the system has been described using the fiber optic indicator 604, one of ordinary skill in the art would readily recognize that any suitable sensor may be used. Once the wrapped sterile dental pack 100 exits the dispensing system storage 502, the sterile dental pack 100 may be collected by the dispensing system output 504 or by the hand of the user.

Figure 7:
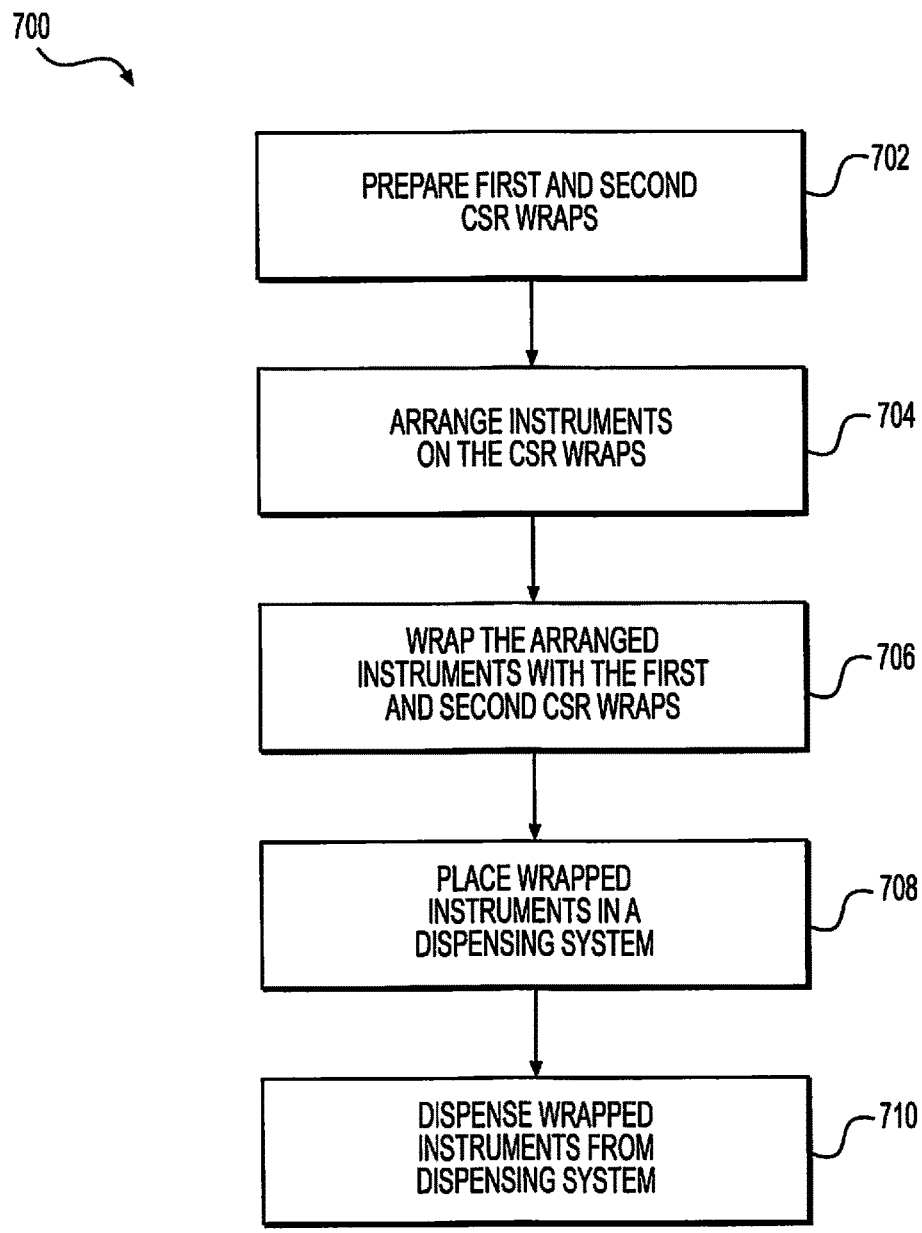
FIG. 7 shows a method for making and delivering the sterile dental pack, according to one aspect of this disclosure.

FIG. 7 shows a method 700 for making and delivering the sterile dental pack 100, according to one aspect of this disclosure. The method 700 may begin at block 702. At block 702, the first CSR wrap 122 and/or the second CSR wrap 124 may be prepared. For example, the first CSR wrap 122 may be laid substantially flat against the second CSR wrap 124, and the first CSR wrap 122 may also be layered with several layers of CSR material creating a cardboard-like tubing, and then rolled around the dental disposable components. One of ordinary skill in the art would readily recognize that any number of CSR wraps may be used. After block 702 is completed, the method 700 may proceed to block 704.

At block 704, various dental disposable supplies may be arranged on the first CSR wrap 124. In one aspect of this disclosure, the dental disposable supplies may be arranged on the first CSR wrap 122. For example, the dental disposable supplies may be the dental disposable supplies described above. Any number of dental disposable supplies may be placed in any arrangement on the first CSR wrap 122. In one aspect of this disclosure, the various dental disposable supplies may be arranged so that they are substantially parallel to each other. After block 704 is completed, the method 700 may proceed to block 706.

At block 706, the arranged dental disposable supplies may be wrapped by the first CSR wrap 122. The CSR wrap 122 and the arranged dental disposable supplies form a cylinder-like structure, as shown in FIG. 3, that is open at the first end 304 and the second end 306. In one aspect of this disclosure, the second CSR wrap 124 may be wrapped around the CSR wrap 122 and dental disposables and is sealed, as shown in FIG. 4; the second CSR wrap 124 may fully wrap the first CSR wrap 122. The ends of second CSR wrap 124 may be sealed with adhesive sterile indicator 302 creating the first end 402 and second end 404 as shown in FIG. 4. Additionally, the adhesive sterile indicator 302 may be used to maintain the cylinder-like structure as well as the thick cardboard-like covering that rolls as a tube creating the first CSR wrap 122. The second CSR wrap 124 may also cover the first end 304 and the second end 306 formed by the first CSR wrap 122. An adhesive, such as adhesive sterile indicator 302, may also be used to maintain the structures formed by the first CSR wrap 122 and the second CSR wrap 124. After block 706 is completed, the method 700 may proceed to block 708.

At block 708, the wrapped dental disposable supplies may be placed within a dispensing system. In one aspect of this disclosure, the dispensing system may be the sterile wrap dispensing system 500 shown in FIG. 5. After block 708 is complete, the method 700 may proceed to block 710.

At block 710, the wrapped dental disposable supplies may be dispensed from the sterile wrap dispensing system 500. In one aspect of this disclosure, a user of the sterile wrap dispensing system 500 may place an object, such as a hand, at an opening of the sterile wrap dispensing system 500. The sterile wrap dispensing system 500 may include a sensor, such as the fiber optic indicator 602. The fiber optic indicator 602 may, upon detecting the hand, dispense a wrapped sterile dental pack 100 from the sterile wrap dispensing system 500. After block 710 is completed, the method 700 may end.

Figure 8:
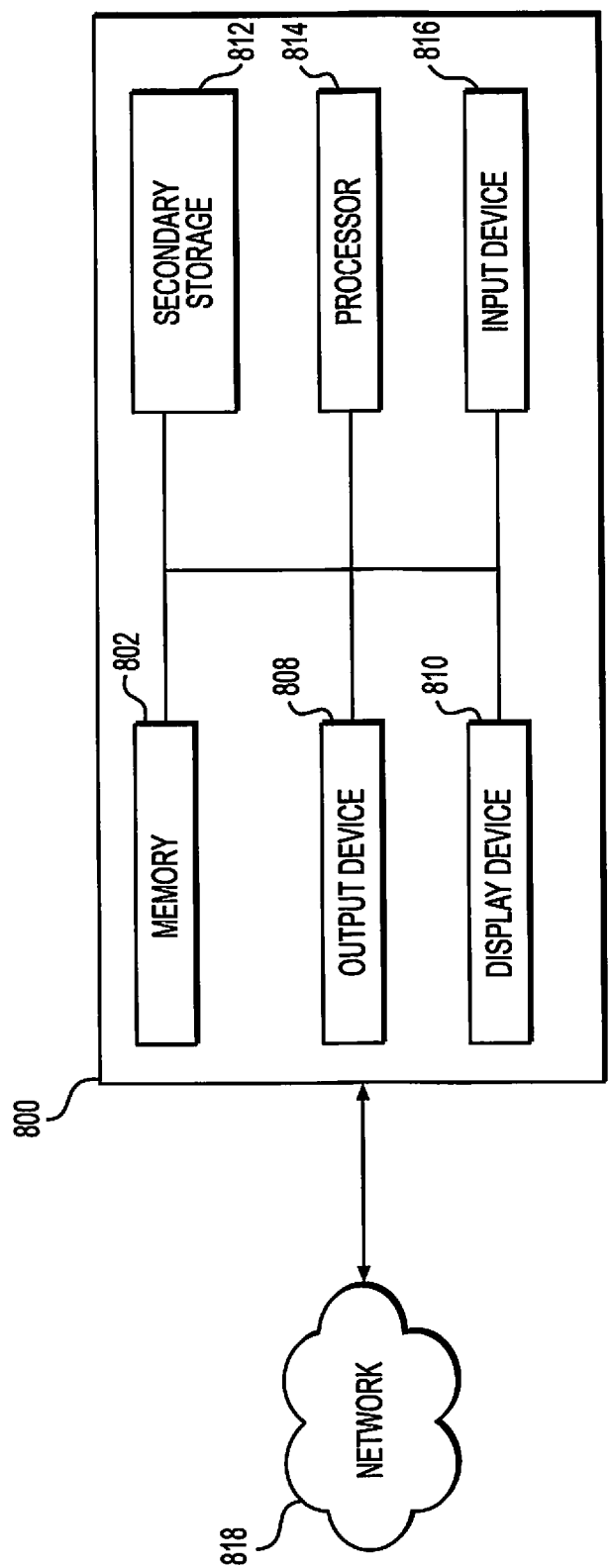
FIG. 8 shows a block diagram illustrating exemplary hardware components that may be used for implementing aspects of the system and method according to one aspect of this disclosure.

FIG. 8 is a block diagram illustrating exemplary hardware components that may be used for implementing aspects of the system and method for providing a wrapped sterile dental pack dispensing system 500. While only one processor 814 is shown in FIG. 8, it is understood that computing systems used to implement the wrapped sterile dental pack dispensing system 500 may include multiple processors.

Computer system 800 typically includes a memory 802, a secondary storage device 812, and a processor 814. Computer system 800 may also include a plurality of processors 814 and be configured as a plurality of, e.g., bladed servers, or other known server configurations. Computer system 800 may also include an input device 816, a display device 810, and an output device 808.

Memory 802 may include RAM or similar types of memory, and it may store one or more applications for execution by processor 814. Secondary storage device 812 may include a hard disk drive, floppy disk drive, CD-ROM drive, or other types of non-volatile data storage. Processor 814 may include multiple processors or include one or more multi-core processors. Any type of processor 814 capable of performing the calculations described herein may be used. Processor 814 may execute the application(s) that are stored in memory 802 or secondary storage 812, or received from the Internet or other network 818. The processing by processor 814 may be implemented in software, such as software modules, for execution by computers or other machines. These applications preferably include instructions executable to perform the functions and methods described above and illustrated in the Figures herein. The applications may provide graphic user interfaces (GUIs) through which users may view and interact with the application(s).

Also, as noted, processor 814 may execute one or more software applications in order to provide the functions described in this specification, specifically to execute and perform the steps and functions in the methods described above. Such methods and the processing may be implemented in software, such as software modules, for execution by computers or other machines.

Input device 816 may include any device for entering information into computer system 800, such as a fiber optic indicator 602, touch-screen, keyboard, mouse, cursor-control device, microphone, digital camera, video recorder, camcorder, or any other suitable sensor. Input device 816 may be used to enter information into GUIs during performance of the methods described above. Display device 810 may include any type of device for presenting visual information such as, for example, a computer monitor or flat-screen display (or mobile device screen). For example, the processor 814 may be operatively coupled to the fiber optic indicator 602. One of ordinary skill in the art would readily recognize that the processor 814 may be operatively coupled to any sensor within, on, or connected to the dispensing system 500. The processor 814 may be configured to determine when to dispense a sterile dental pack 100. For example, if the fiber optic indicator 602 senses an object, such as a hand, for a pre-determined amount of time, such as 1 second, the processor 814 may determine that a sterile dental pack 100 should be dispensed. Additionally, or alternatively, the processor 814 may be coupled to another sensor, such as a proximity sensor, to determine a number of sterile dental packs 100 available for dispensing, for example. Alternatively, the processor 814 may determine if there are any sterile dental packs 100 remaining in the dispensing system 500. Additionally, or alternatively, the processor 814 may monitor various sensors to determine a status of the dispensing system 500. The processor 814 may determine if the dispensing system 500 is functioning correctly or if there is a component that is malfunctioning, for example. The processor 814 may communicate with a supplier or manufacturer, for example, over or via network 818. For example, the processor 814 may communicate with a supplier to order sterile dental packs 100 if the number of sterile dental packs 100 in the dispensing system 500 is low or empty. Additionally, or alternatively, the processor 814 may communicate with a manufacturer to request maintenance if the dispensing system 500 is not functioning properly.

Output device 808 may include any type of device for presenting a hard copy of information, such as a printer, and other types of output devices include speakers or any device for providing information in audio form.

Examples of computer system 800 include dedicated server computers, such as bladed servers, personal computers, laptop computers, notebook computers, palm top computers, network computers, mobile devices, or any processor-controlled device capable of executing a web browser or other type of application for interacting with the system.

Although only one computer system 800 is shown in detail, the wrapped sterile dental pack dispensing system 500 may use multiple computer systems or servers as necessary or desired to support the users, as described above. In addition, although computer system 800 is depicted with various components, one skilled in the art will appreciate that the computer system 800 can contain additional or different components. In addition, although aspects of an implementation consistent with the above are described as being stored in memory, one skilled in the art will appreciate that these aspects can also be stored on or read from other types of computer program products or computer-readable media, such as secondary storage devices, including hard disks, floppy disks, or CD-ROM; or other forms of RAM or ROM. Computer-readable media may include instructions for controlling a computer system, such as the computer system 800, to perform a particular method, such as methods described above.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A sterile dental pack comprising:
a first wrap;
a second wrap; and
a plurality of dental disposable supplies arranged on top of the second wrap,
wherein the second wrap partially encloses the plurality of dental disposable supplies; and
wherein the first wrap completely encloses the second wrap, wherein the first wrap is sealed to itself to form an airtight container, wherein
the plurality of dental disposable supplies comprising at least one of cotton applicator sticks, one or more gauzes, cotton pellets, cotton rolls, air water syringes, surgical suction tips, high volume suction tips, saliva ejectors, dry aids, tongue depressors or one or more wraps.

2. The sterile dental pack of claim 1, wherein the dental disposable supplies are arranged so that the dental disposable supplies are substantially parallel.

3. The sterile dental pack of claim 1, wherein the first wrap and second wrap are made of CSR material.

4. The sterile dental pack of claim 1, further comprising an adhesive to join two ends of the first wrap or the second wrap together.

5. The sterile dental pack of claim 1, wherein the first wrap and the second wrap are biodegradable.

6. The sterile dental pack of claim 1, wherein the plurality of dental disposable supplies are sterilized.

7. A method for forming a sterile dental pack, the method comprising:
preparing a first wrap and a second wrap;
arranging a plurality of dental disposable supplies on the first wrap; and wrapping the plurality of dental disposable supplies within the first wrap and the second wrap, wherein the first wrap is sealed to itself to form an airtight container, wherein the plurality of dental disposable supplies comprising at least one of cotton applicator sticks, one or more gauzes, cotton pellets, cotton rolls, air water syringes, surgical suction tips, high volume suction tips, saliva ejectors, dry aids, tongue depressors or one or more wraps.

8. The method of claim 7, wherein the plurality of dental disposable supplies are arranged so that the dental disposable supplies are substantially parallel.

9. The method of claim 7, wherein the first wrap and the second wrap are made of CSR material.

10. The method of claim 7, further comprising appending an adhesive to join two ends of the first wrap or the second wrap together.

11. The method of claim 7, wherein the first wrap and the second wrap are biodegradable.

12. The method of claim 7, wherein the plurality of dental disposable supplies are sterilized.

* * * * *